US00PP18730P3

(12) United States Plant Patent
Leis et al.

(10) Patent No.: US PP18,730 P3
(45) Date of Patent: Apr. 15, 2008

(54) APPLE TREE NAMED 'CIVG198'

(50) Latin Name: *Malus domestica Mill.*
Varietal Denomination: CIVG198

(75) Inventors: Michelangelo Leis, Ferrara (IT); Gianfranco Castagnoli, Quingentole (IT); Alessio Martinelli, Gaibanella (IT); Francesco Tagliani, Argenta (IT)

(73) Assignee: Consorzio Italiano Vivaisti, S. Giuseppe Di Comacchio (FE) (IT)

( * ) Notice: Subject to any disclaimer, the term of this patent is extended or adjusted under 35 U.S.C. 154(b) by 53 days.

(21) Appl. No.: 11/342,555

(22) Filed: Jan. 31, 2006

(65) Prior Publication Data

US 2006/0191048 P1 Aug. 24, 2006

(30) Foreign Application Priority Data

Nov. 7, 2007 (QZ) ..... PBR 2005/0312

(51) Int. Cl.
*A01H 5/00* (2006.01)

(52) U.S. Cl. ..... Plt./161
(58) Field of Classification Search ..... Plt./161
See application file for complete search history.

(56) References Cited

PUBLICATIONS

Official Gazette of the Community Plant Variety Office (CPVO) dated Apr. 15, 2005, listing assigned Application Number and Variety Denomination to corresponding international application, CPVO 2005/0312 filed Feb. 21, 2005, together with Assignee and Inventors' information. (6 pgs).

Sansavini, et al. 2004. Grandi aspettative per i programmi di miglioramento genetico del melo pubblici e private operative in Italia. *Frutticoltura.* No. 11, pp. 18–30 (pp. 18 and 30 attached—specific paragraph of relevance on p. 30, *Selezioni in fase di pre–licenziamento*).

Martinellia, et al. 2005. Problematiche vivaistiche e competizione frutticola in Europa: le innovazioni messe in atto dal CIV. *Fruitticoltura. No.* 12, pp. 37–40 (specific paragraph of relevance on p. 40).

*Primary Examiner*—Kent Bell
*Assistant Examiner*—June Hwu
(74) *Attorney, Agent, or Firm*—Foley & Lardner LLP

(57) ABSTRACT

A new and distinct *Malus domestica Mill,* apple tree variety named 'CIVG198' particularly characterized by having deep, red skin color, high sugar content, very firm flesh, scab resistance, long storage capacity and long shelf life.

7 Drawing Sheets

PRIORITY CLAIM

This application claims priority under 35 U.S.C. §119(f) of the European Community Plant Variety Rights No. 2005/0312 filed Feb. 21, 2005.

Latin name of the genus and species of the plant claimed: *Malus domestica Mill.*

Variety denomination: 'CIVG198'.

BACKGROUND OF THE INVENTION

The present invention relates to a new and distinct variety of apple tree, botanically known as *Malus domestica Mill.* of the Family Rosaceae, and hereinafter referred to by the variety denomination 'CIVG198'.

The new *Malus* variety is a product of a planned breeding program conducted by the inventors, Michelangelo Leis, Alessio Martinelli, Gianfranco Castagnoli and Francesco Tagliani in S. Giuseppe di Comacchio (Ferrara), Italy. The objective of the breeding program was to develop a new *Malus* variety with deep, red skin color, high sugar content, very firm flesh, scab resistance, long storage capacity and long shelf life.

The new *Malus* variety, 'CIVG198', originated from a cross made in a planned, controlled breeding program in S. Giuseppe di Comacchio (Ferrara), Italy. The female parent is *Malus domestica Mill.* 'Gala' ('Kidd's Orange'×'Golden Delicious' — 1939, patented, U.S. Plant Pat. No. 3,637). The male parent is *Malus domestica Mill.* 'Liberty' (unpatented, 'Macoun'×Purdue 54-12-1955). 'CIVG198' was discovered and selected in 1996 by the inventors as a flowering plant within the progeny of the stated cross in a controlled environment in S. Guiseppe di Comacchio (Ferrara), Italy.

Asexual reproduction of the new *Malus* variety by budding and grafting as first performed in September, 1996, and then again in September, 1999, and in the following years in S. Giuseppe di Comacchio (Ferrara), Italy, and has demonstrated that the combination of characteristics as herein disclosed for the new *Malus* variety are firmly fixed and retained through successive generations of asexual reproduction. The new variety reproduces true to type.

BRIEF DESCRIPTION OF THE INVENTION

The following traits have been repeatedly observed and are determined to be unique characteristics of 'CIVG198' which in combination distinguish this apple tree as a new and distinct variety:

1. Deep red skin color of the fruit;
2. High sugar content;
3. Very firm flesh;
4. Scab resistance;
5. Long storage capacity; and
6. Long shelf life.

In comparison to the parental varieties, 'Gala' and 'Liberty', 'CIVG198' differs primarily in the traits listed in Table 1:

TABLE 1

| Variety | Time of maturity for consumption | Flesh firmness | Fruit shape |
|---|---|---|---|
| 'CIVG198' | Medium | Very strong | Conic |
| 'Gala' | Early | Strong | Globose conical |
| 'Liberty' | Early | Medium | Globose |

Of the commercial cultivars known to the inventors, the most similar in comparison to 'CIVG198' is the male parental variety 'Liberty' as compared in Table 1.

BRIEF DESCRIPTION OF THE DRAWINGS

The accompanying photographs illustrated the overall appearance of the new apple tree 'CIVG198' showing the colors as true as is reasonably possible with color reproductions of this type. Color in the photographs may differ slightly from the color value cited in the detailed botanical description, which accurately describe the color of 'CIVG198'.

1)

2)

3)

4)

5)

6)

7)

DETAILED BOTANICAL DESCRIPTION

Figure 1:
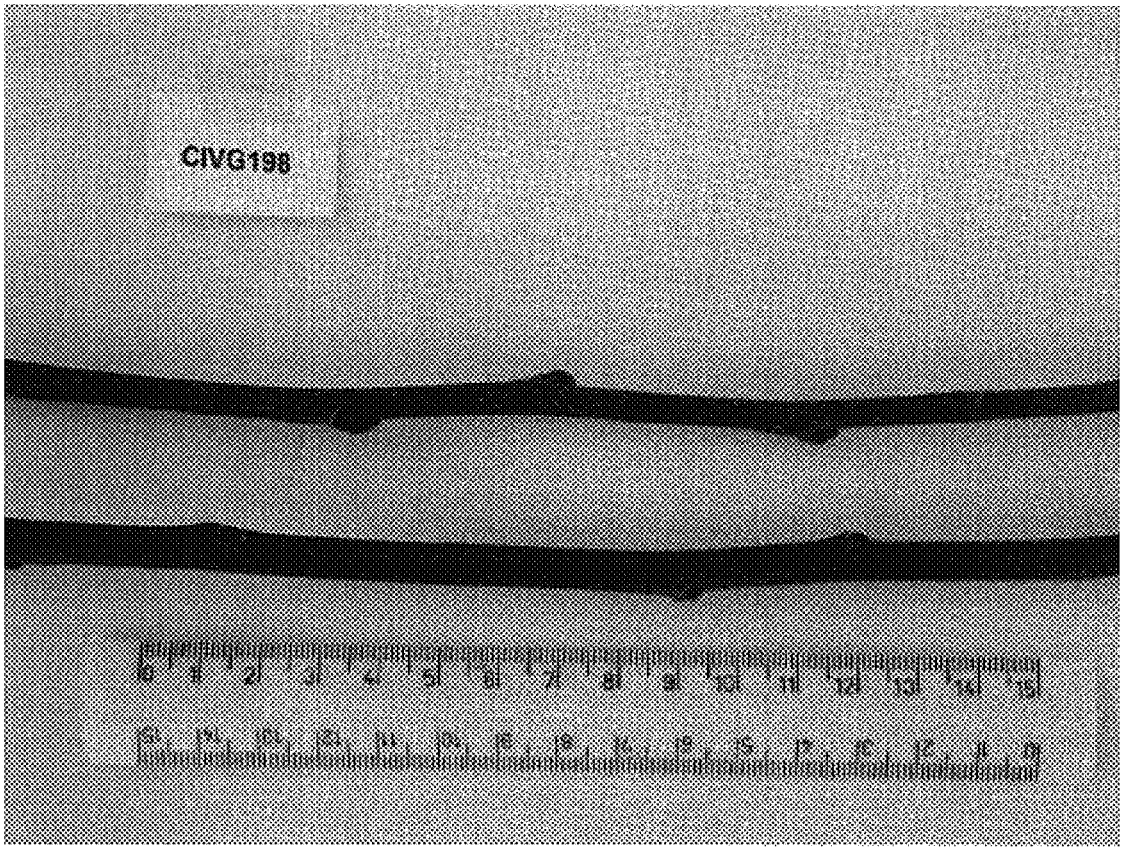
FIG. 1 shows dormant wood of 'CIVG198'.
Figure 2:
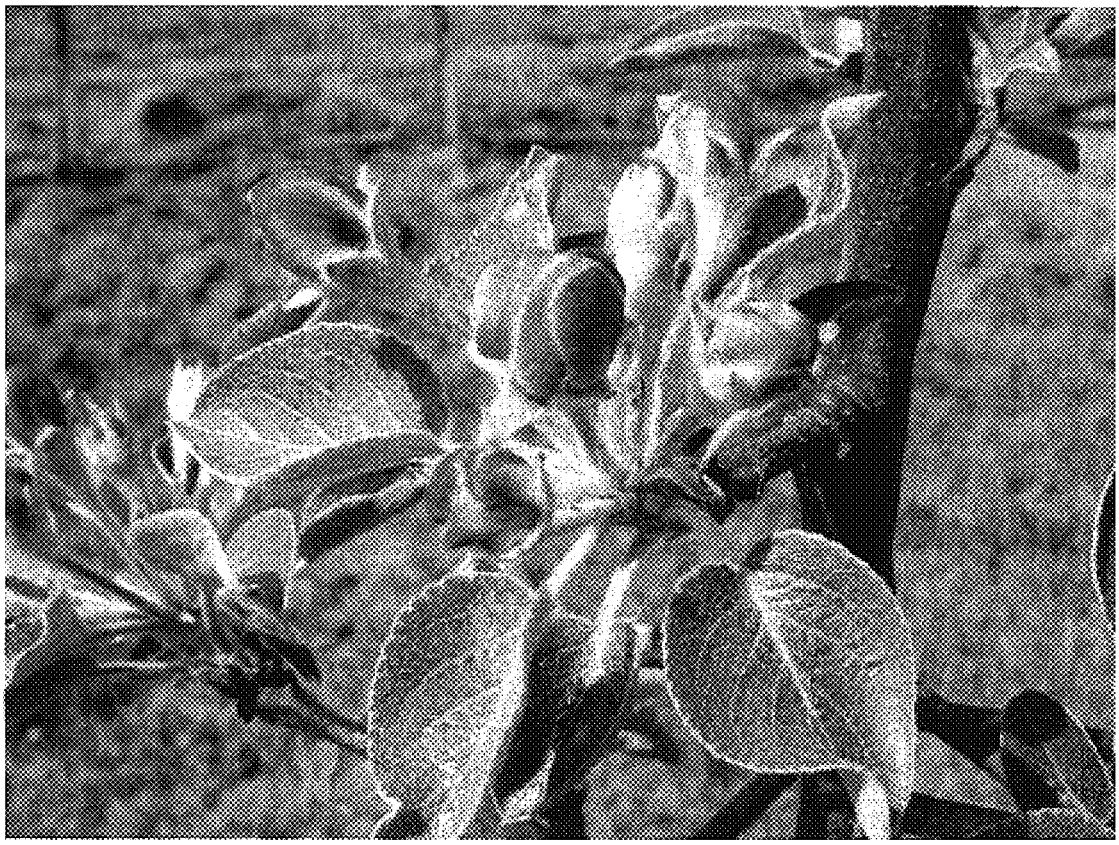
FIG. 2 shows typical inflorescence and leaves of 'CIVG198'.
Figure 3:
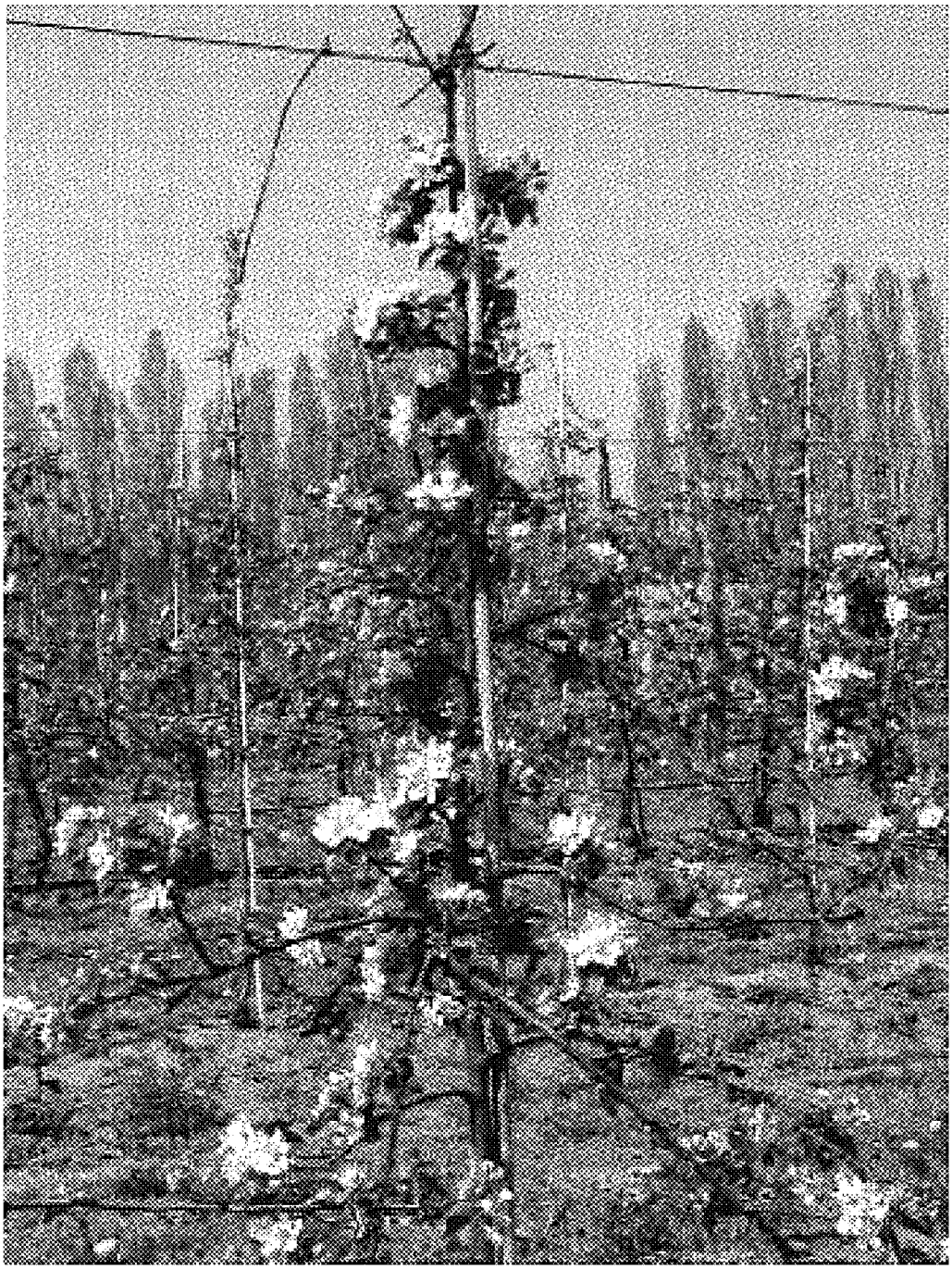
FIG. 3 shows a blooming tree of 'CIVG198'.
Figure 4:
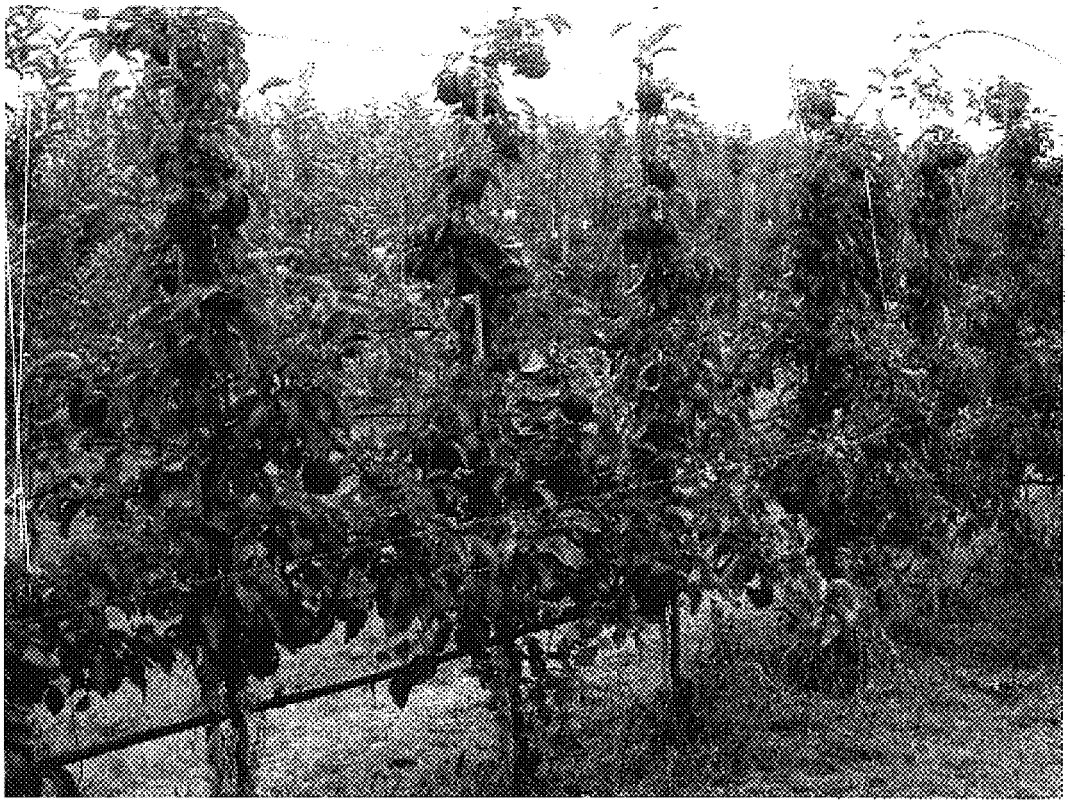
FIG. 4 shows a bearing tree of 'CIVG198'.
Figure 5:
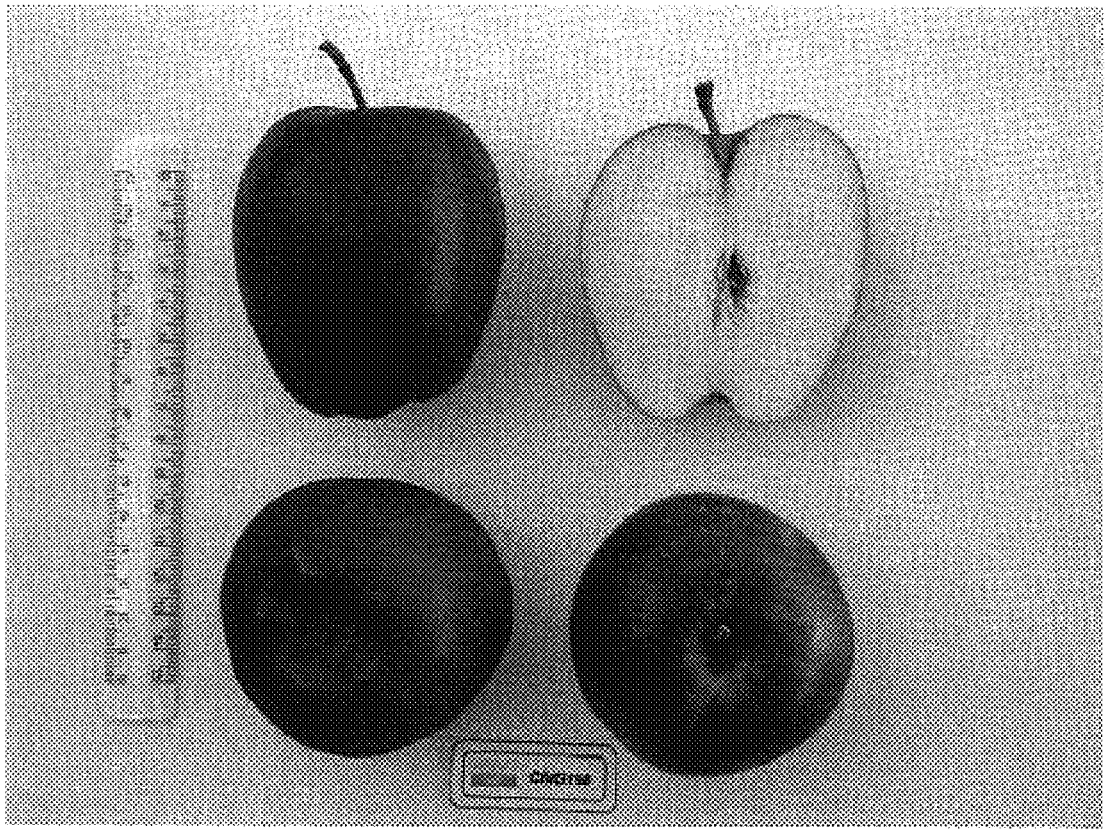
FIG. 5 shows different images of the typical fruit of 'CIVG198'.
Figure 6:
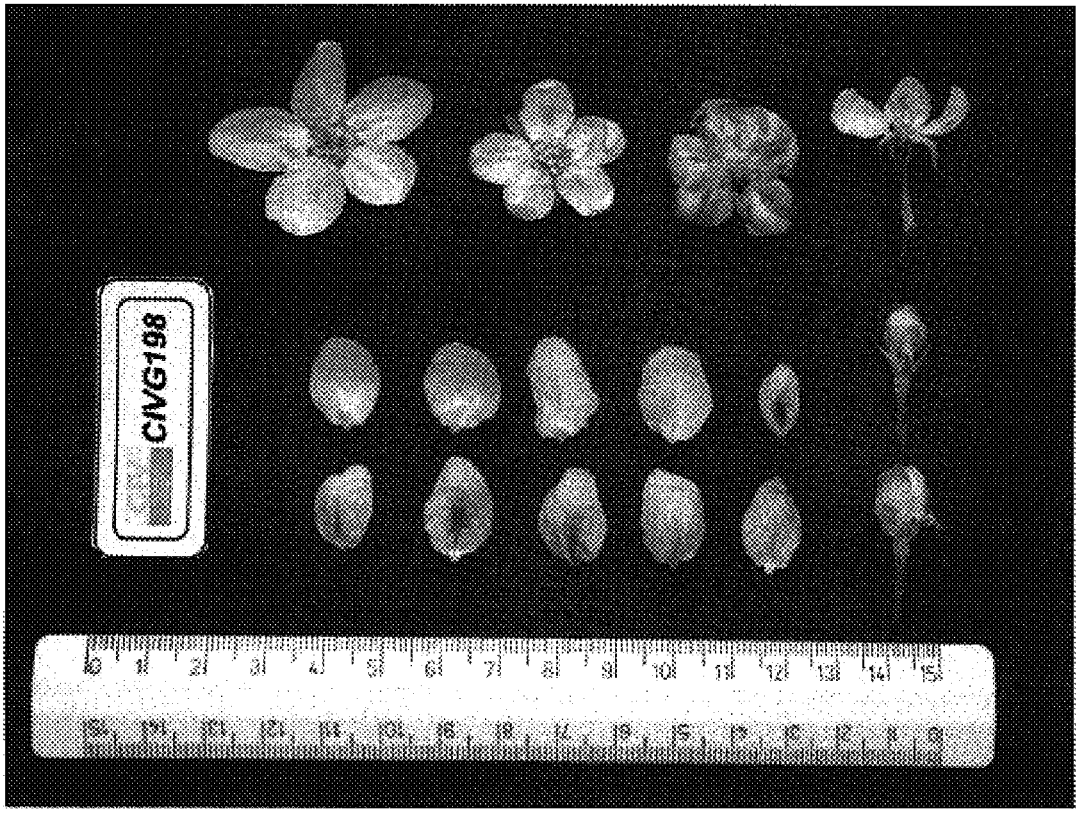
FIG. 6 shows different images of the flowers of 'CIVG198'.
Figure 7:
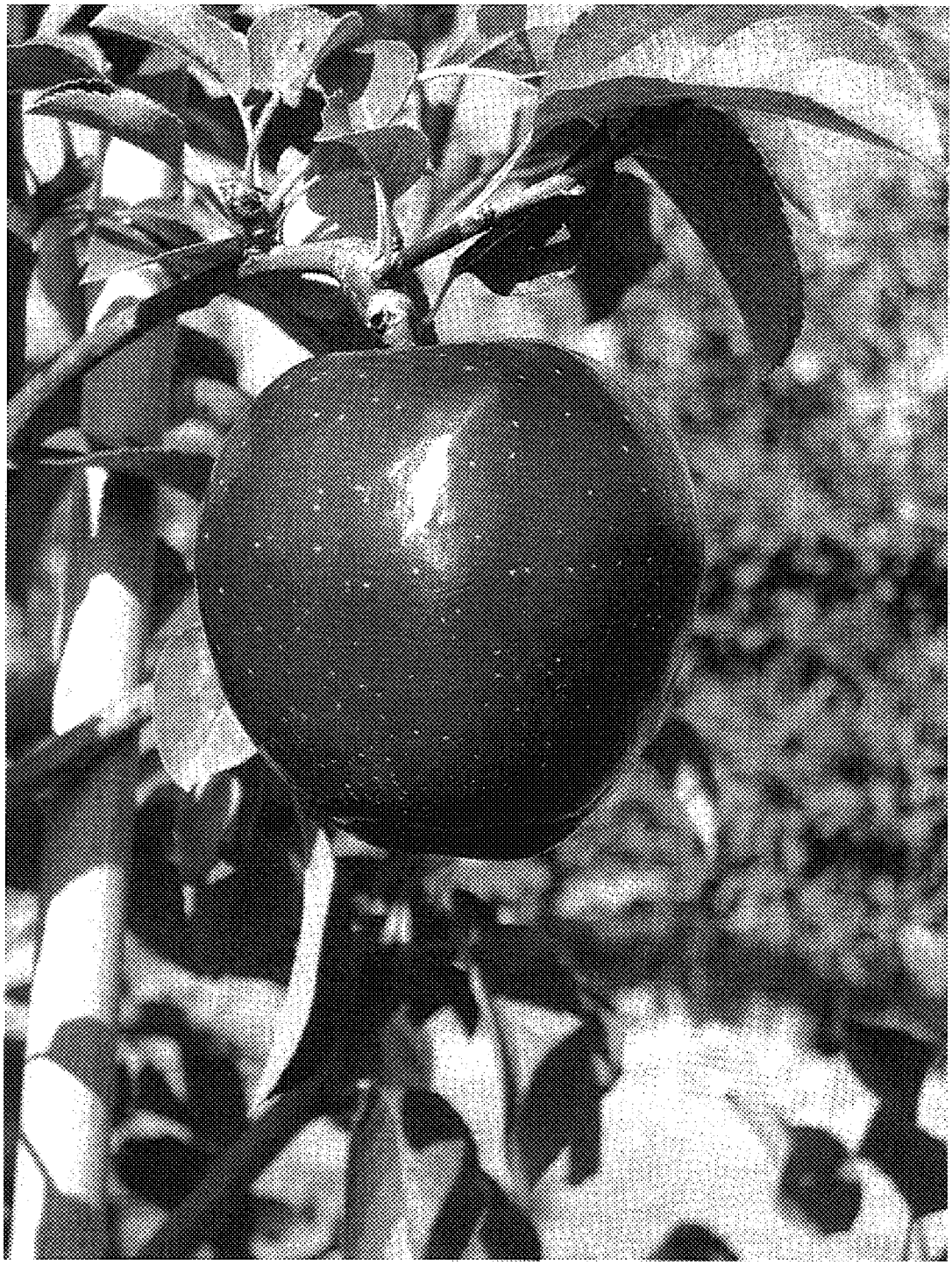
FIG. 7 shows a close-up view of a mature fruit attached to a 'CIVG198' tree.

The new *Malus* variety 'CIVG198' has not been observed under all possible environmental conditions. The phenotype of the new variety may vary with variations in environment such as temperature, light intensity, and day length without any change in the genotype of the plant.

The aforementioned photographs, together with the following observations, measurements and values describe the new *Malus* variety 'CIVG198' as grown in the apple farm in S. Guiseppe di Comacchio (Ferrara), Italy, under conditions which closely approximate those generally used in commercial practice. The apple farm where 'CIVG198' is grown is situated near the Adriatic sea (44°45' North, 12°11' East) and is zero (0) meters above sea level. The soil of the apple farm where 'CIVG198' is grown is sandy, and the soil is treated with manure every year and irrigated with drip irrigation systems. The climate is temperature continental with high summer temperatures and low winter temperatures.

Unless otherwise stated, the detailed botanical description includes observations, measurements and values based on four (4) year old 'CIVG198' trees that were grown in the apple farm in S. Guiseppe di Comacchio (Ferrara), Italy, from 2003 to 2004. All trees were of cropping maturity. Quantified measurements are expressed as an average of measurements taken from a number of individual trees of 'CIVG198'. The measurements of any individual tree, or any group of trees, of the new variety may vary from the stated average.

Color references are made to the Royal Horticultural Society Colour Chart (RHS), except where general colors of ordinary significance are used. Color values were taken under daylight conditions at approximately at 10:00 am in S. Guiseppe di Comacchio (Ferrara), Italy.

At trees of 'CIVG198', insofar as they have been observed, have been identical in all the characteristics described below.

Classification: Botanical: *Malus domestica Mill.*

Parentage:

*Female parent.*—*Malus domestica Mill.* 'Gala' (patented).

*Male parent.*—*Malus domestica Mill.* 'Liberty' (unpatented).

Propagation: Budding and grafting on M9 rootstock.

Tree:

*Age.*—Observed plants were four years old.

*Vigor.*—Average vigor.

*Form.*—Pyramidal.

*Habit.*—Upright, branches angle is 70° to 80° with respect to trunk if allowed to grow naturally.

*Density.*—Medium density.

*Cropping behavior.*—Early beginning of production; very high and constant productivity and regular and abundant flowering; no biennial bearing.

*Type of bearing.*—Long shoot and spurs.

*Production.*—$4^{th}$ year: 22 Kg.

*Size.*—Height: 2.28 m. Spread: 1.20 m. Trunk Diameter: 28.8 mm as measured 20 cm above point of grafting.

*Surface texture.*—Smooth.

*Bark color.*—Brown, RHS 166A.

*Trunk lenticels.*—Length: 2.64 mm. Width: 0.99 mm. Color: Yellow-brown, RHS 164B. Density: About 3 per $cm^2$.

*Branches.*—Number per tree: About twenty (20). Length: Varies due to pyramidal shape of tree. At 4 years, maximum of 100 cm to 110 cm; minimum of 10 cm to 12 cm. Diameter (at 3 years): About 9 mm to 11 mm. Surface texture: Smooth. Color (at 3 years): RHS 176A, (greyed-orange group). Internode length: About 2 to 5 cm. Internode diameter: About 9 mm to 11 mm.

*Branches lenticels.*—Length: 1.0 mm. Width: 0.4 mm. Color: Yellow-Grown, RHS 164B. Density: About 5 per $cm^2$.

Leaves:

*Arrangement.*—Alternate, simple, petiolated.

*Lamina.*—Size: Length (4 year old): 98.8 mm (from $3^{rd}$ to $5^{th}$ fully expanded leaf). Width (4 year old): 60.4 mm (from $3^{rd}$ to $5^{th}$ fully expanded leaf). Length/width ratio: 1.64. Overall Shape: Elliptical-elongated. Base shape: Obtuse. Apex shape: Acuminate. Margin: Bluntly serrate. Pubescence: Absent on upper surface and lightly pubescent on lower surface. Attitude in relation to shoot: Outwards. Color (mature leaves): Green, RHS 137 A. Color (immature leaves): Yellow-Green, RHS 144 B.

*Venation.*—Type: Prominent pinnate venation from central vein to the leaf edge. Color: Light green, RHS 139 D.

*Petiole.*—Length: 43.1 mm. Diameter: 1.64 mm. Texture: Hairy. Color: Light green, RHS 138 B.

*Stipule.*—Arrangement: Adnate. Length (distance of stipules from basal attachment of petiole): Short, 0 mm to 0.5 mm. Width: 0.7 mm to 1.2 mm.

Spur:

*Present.*—Yes.

*Distance between each spur.*—On the three year old branches, the distance is about 20 mm to 50 mm.

*Number of fruit per spur.*—2 to 4.

Flowers:

*Blooming time.*—Full bloom on April 16$^{th}$.

*Blooming period.*—10 to 12 days.

*Fragrance.*—Very slight.

*Type.*—Inflorescence.

*Number of flowers per inflorescence.*—5 to 6.

*Flower size.*—Diameter: 35.5 mm. Flower color: Primarily white-pink, RHS 69 D, when petals fully opened, but undersides of petals light red-purple color, RHS 63B, making pink blooming stage pink.

*Buds.*—Number of buds per spur: one (1). Shape: Pointed. Length: 9.1 mm. Width: 4.98 mm. Color: Dark purple-brown, RHS value 187 A.

*Petals.*—Arrangement: Intermediate. Number per flower: Five to six (5 to 6). Length: 19.54 mm. Width: 13.41 mm. Length/width ratio: 1.46. Overall shape: Ellipsoid. Apex shape: Obtuse. Base shape: Obtuse. Texture: Smooth. Margin: Slightly crenate. Color (upper surface): White-pink, RHS 69D. Color (lower surface): Light red-purple, RHS 63B.

*Sepals.*—Number per flower: Five to six (5 to 6). Length: 7.71 mm. Width: 3.54 mm. Length/width ratio: 2.2. Overall shape: Lanceolate. Apex shape: Acute. Texture: Hairy. Margin: Entire. Color: Length green, RHS 139C.

*Pedicel.*—Length: 13 mm to 15 mm. Diameter: 2.0 to 2.5 mm. Texture: Hairy. Color: Light green, RHS 139C.

Fruit:

*Keeping quality.*—The fruit keeps very well on the tree. It can be stored in cold temperature conditions for up to seven months without loosing firmness and juiciness. It has a long shelf life, up to three weeks without loosing firmness and juiciness.

*Maturity when described.*—Ripe for eating.

*Maturity period after full bloom.*—About 147 days after full bloom (April 16$^{th}$).

*Date of first and last pickings* (*harvest*).—About September 06$^{th}$ and September 15$^{th}$ in S. Giuseppe di Comacchio (Ferrara) Italy (North 44°45'46.2", East 012°11'31.9") in year 2005.

*General shape.*—Conic.

*Average weight.*—205.03 g.

*Fruit size.*—Average height: 76.44 mm. Average diameter (at widest point): 75.23 mm.

*Position of maximum diameter.*—¾ of the height near stem end.

*Height/thickness ratio.*—1.02.

*Stem.*—Length: 23.34 mm. Diameter: 2.94 mm. Color: Green, RHS 144A.

*Stalk cavity.*—Depth: 14.75 mm. Width: 34.1 mm.

*Eye basin.*—Depth: 9.1 mm. Width: 31.7 mm. Crowning at calyx end: Weak. Position of sepals: Half-closed. Calyx tube: Funnel-form.

*Skin.*—Thickness: Thick. Texture: Smooth. Bloom: Absent. Greasiness: Weak or absent. Firmness (at picking time): 9.5 to 10 kg/cm$^2$. Overcolor color: Deep red (dark greyed-purple group), RHS value 187B. Percentage of skin surface with overcolor color: 85–95%. Pattern of overcolor: Solid flush. Intensity of overcolor: High; very bright. Ground color: Greyed-Yellow, RHS value 160B.

*Skin lenticels.*—Length: About 0.38 mm. Width: About 0.39 mm. Color: RHS 164C. Density: About 8 per cm$^2$.

*Flesh.*—Color: Yellow-white, RHS 158A. Texture: Firm, crisp and juicy. Aroma: Medium light intensity, slightly acidic. Eating quality: Good with high level of sugar and acidity. Sugar content (at picking time): 14 to 15 Brix. Acidity/Starch (at picking time): Acidity: 7 to 7.5 g/lt Malic acid/starch: 3 (scale 1 to 5).

*Core.*—Symmetry of core: Big and symmetric. Distinctness of core lines: Medium — strong. Locules: Number (per fruit): 5. Length: 10.6 mm. Width: 4.5 mm. Form: Partly open.

Seeds:

*Number per fruit.*—8 to 10.

*Number per locule.*—About 2.

*Shape.*—Ellipsoid, elongated and pointed.

*Length.*—9.7 mm.

*Width.*—5.2 mm.

*Color.*—Brown, RHS 200D.

Reproductive organs:

*Androecium.*—Stamens: Number per flower: 17.9. Length: 10.31 mm. Filament: Length: 8.56 mm. Anther: Shape: Ovoid, flat in the center. Length: 2.21 mm. Diameter: 1.75 mm. Color: Pale yellow, RHS 11B. Pollen: Amount: Abundant. Color: Pale yellow, RHS 11B. Requirements: Gala, Golden and Granny Smooth are good pollinators.

*Gynoecium.*—Stigma: Shape: Bulbous on top. Length: 0.86 mm. Width: 0.43 mm. Color: Green, RHS 134A. Style: Number per flower: 5. Length: 11.32 mm. Width: 0.28 mm. Color: Yellow-Green, RHS 150C. Ovary: Length: 2.82 mm. Width: 1.98 mm. Color: Yellow-green, RHS 144A.

*Use.*—Fresh market.

*Sensitivity to disease/pests.*—Scab resistance.

Winter hardiness: Tolerance to temperatures of −12° C. without observed damage to wood and buds of dormant apple trees; but open flowers and young fruitlets are killed by exposure to −3° C. to −5° C., depending on the length of exposure.

Drought/heat tolerance: Good tolerance to heat, up to 40° C., growth is limited by drought periods without irrigation.

Shipping/storage characteristics: Little sensitivity to bruising; very good storability under ULO-conditions (1° C., 2% $O_2$, 2% ($CO_2$) for up to seven (7) months.

We claim:

1. A new and distinct *Malus domestica Mill.* apple tree variety named 'CIVG198', substantially as illustrated and described herein.

* * * * *

UNITED STATES PATENT AND TRADEMARK OFFICE

CERTIFICATE OF CORRECTION

PATENT NO. : PP 18,730 P3
APPLICATION NO. : 11/342555
DATED : April 15, 2008
INVENTOR(S) : Michelangelo Leis et al.

It is certified that error appears in the above-identified patent and that said Letters Patent is hereby corrected as shown below:

Title Page Item (30), Foreign Application Priority Data:

Please delete [November 7, 2007] and replace it with February 21, 2005.

Signed and Sealed this

Eighth Day of July, 2008

JON W. DUDAS
*Director of the United States Patent and Trademark Office*